US008044376B2

(12) United States Patent
Smirnov (10) Patent No.: US 8,044,376 B2
(45) Date of Patent: Oct. 25, 2011

(54) DEVICES AND METHODS FOR PROTECTION AGAINST EXPOSURE TO ELECTROMAGNETIC RADIATION

(76) Inventor: Igor Smirnov, San Marcos, CA (US)

( * ) Notice: Subject to any disclaimer, the term of this patent is extended or adjusted under 35 U.S.C. 154(b) by 241 days.

(21) Appl. No.: 12/319,398

(22) Filed: Jan. 7, 2009

(65) Prior Publication Data

US 2010/0171051 A1    Jul. 8, 2010

(51) Int. Cl.
*G21F 3/02*    (2006.01)
(52) U.S. Cl. ............... 250/505.1; 250/515.1; 250/518.1; 250/519.1
(58) Field of Classification Search ............... 250/505.1, 250/515.1, 518.1, 519.1
See application file for complete search history.

(56) References Cited

U.S. PATENT DOCUMENTS 6,022,479 A * 2/2000 Smirnov ................ 210/695
6,369,399 B1   4/2002 Smirnov

OTHER PUBLICATIONS

Smirnov, Polymer Material Providing Compatibilty Between Technologically Originated EMR and Biological Systems, Explore! 15(4):1-8 (2006).

Lai, Interaction of microwaves and a temporally incoherent magnetic field on spatial learning in the rat, Physiology & Behavior 2004; 82:785-789.
Lin et al., Electric and magnetic noise blocks the 60 Hz magnetic field enhancement of steady state c-myc transcript levels in human leukemia cells, Bioelectrochemistry and Bioenergenetics 1995; 36:33-37.
Litovitz et al., The role of coherence time in effect of microwaves on ornithine decarboxylase activity, Bioelectromagnetics, 1993; 14:395-403.
Litovitz et al, Bioeffects induced by exposure to microwaves are mitigated by superposition of ELF noise, Bioelectromagnetics, 1997; 18:422-430.
Mullins et al., Simultaneous application of a spatially coherent noise field blocks response of cell cultures to a 60 Hz electromagnetic field, 1993, San Francisco Press, Inc. San Francisco, CA.

* cited by examiner

*Primary Examiner* — David A Vanore
(74) *Attorney, Agent, or Firm* — Biotech Beach Law Group PC (57) ABSTRACT

The present invention provides devices and methods that protect against exposure to remote sources of electromagnetic radiation (EMR). As such, the devices provide protection against a plurality of electrical equipment used in ordinary households and employment settings. The device includes a housing, a solenoid operably connected to a driver and a polymer. The solenoid generates incident radiation which results in the polymer emitting electromagnetic oscillations at frequencies that counter adverse effects associated with the subject's exposure to the electromagnetic radiation.

8 Claims, 8 Drawing Sheets

Left image Control 1                          Right Image RF Phone No MARNE

| | Control 1 | | TREO- NO MARNE | | |
|---|---|---|---|---|---|
| | Values | Norms | Values | Norms | Units |
| I | 18.8 | 8.3-18.2 | 22.10 | 8.3-18.2 | μA |
| iR | 68.00 | 71.2-162.0 | 60.50 | 71.2-162.0 | kOhm |
| iC | 14.71 | 6.2-14.0 | 16.53 | 6.2-14.0 | $10^{-6}$ S/m |
| ipH | 7.353 | 7.31-7.35 | 7.359 | 7.31-7.35 | I.U |
| icpH | 6.997 | 7.00-7.04 | 6.991 | 7.00-7.04 | I.U |
| tVO2 | 52.3 | 48-52 | 52.9 | 48-52 | % |
| tO2 | 77.7 | 78-82 | 77.1 | 78-82 | mm/Hg |
| tCO2 | 48.3 | 44-48 | 48.9 | 44-48 | mm/Hg |
| ATP | 55.8 | 45-55 | 57.2 | 45-55 | % |
| A.C.H. Pressure | 37.3 | 33-37 | 37.9 | 33-37 | mm/Hg |
| Blood Viscosity | 5.1 | 4-5 | 5.2 | 4-5 | $10^{-4}$ Pa/s |
| I Oncotic forces | 2.8 | 2.8-3.2 | 2.7 | 2.8-3.2 | mm/Hg |
| Water content | 17.2 | 15-17 | 17.4 | 15-17 | % |

Neuronal Excitability: Increased                Neuronal Excitability: Increased
Sympathetic system (C8-L4) - Norms          Sympathetic system (C8-L4) - Reduced

FIG. 3A

| Control 2 | | | TREO- with MARNF | | | |
|---|---|---|---|---|---|---|
| | Values | Norms | Values | Norms | Units | |
| iI | 19.9 | 8.3-18.2 | 17.00 | 8.3-18.2 | µA | |
| iR | 65.5 | 71.2-162.0 | 77.60 | 71.2-162.0 | kOhm | |
| iC | 15.27 | 6.2-14.0 | 12.89 | 6.2-14.0 | 10-6 S/m | |
| ipH | 7.354 | 7.31-7.35 | 7.35 | 7.31-7.35 | I.U | |
| icpH | 6.996 | 7.00-7.04 | 7.00 | 7.00-7.04 | I.U | |
| tVO2 | 52.4 | 48-52 | 51.6 | 48-52 | % | |
| tO2 | 77.6 | 78-82 | 78.4 | 78-82 | mm/Hg | |
| tCO2 | 48.4 | 44-48 | 47.6 | 44-48 | mm/Hg | |
| ATP | 56.0 | 45-55 | 54.0 | 45-55 | % | |
| A.C.H. Pressure | 37.4 | 33-37 | 36.6 | 33-37 | mm/Hg | |
| Blood Viscosity | 5.1 | 4-5 | 4.9 | 4-5 | 10-4 Pa/s | |
| I Oncotic forces | 2.8 | 2.8-3.2 | 2.8 | 2.8-3.2 | mm/Hg | |
| Water content | 17.2 | 15-17 | 16.8 | 15-17 | % | |

Neuronal Excitability: Increased        Neuronal Excitability: Norms

Sympathetic system (C8-L4) - Reduced    Sympathetic system (C8-L4) – Norms

FIG 4A: Phantom Head Without MRET Random Field Generator (MARNF)

FIG 4B: Phantom Head With MRET Random Field Generator (MARNF)

DEVICES AND METHODS FOR PROTECTION AGAINST EXPOSURE TO ELECTROMAGNETIC RADIATION

TECHNICAL FIELD

The present invention relates to devices and methods for protection against exposure to electromagnetic radiation and more specifically to a stand alone device that generates protective frequencies by inducing the oscillation of a polymer at frequencies that counter adverse effects associated with electromagnetic radiation.

BACKGROUND OF THE INVENTION

Every operating electrical and electronic device emits electromagnetic radiation (EMR). The power of this emission varies depending on the size and electrical strength of the device and the electrical current it carries. High voltage power lines are significant emitters, and their field strength is sufficiently high to cause adverse effects on humans, animals and plants even hundreds of feet away. Smaller devices, such as computers, television sets, cellular phones and microwaves, emit lesser quantities of EMR, but the effect on humans can still be significant because people are in much closer proximity to such devices.

Adverse effects on the health of humans that have been reported as attributable to long-term EMR exposure include occurrence of certain cancers, multiple sclerosis, headache, and sleep disruption, impairment of short term memory, autism, and significant increases in the frequency of seizures in epileptic children. Reported adverse effects on animals have included stillbirths of young and reduction of milk production in cattle.

Although the effects of electromagnetic radiation on human health are not always easily quantifiable it is the desire of many prudent people to eliminate or reduce their exposure to EMR. There exist various methods of protecting from EMR that rely on reducing the magnitude (or strength) of the radiation that enters human body. Most commonly these utilize some sort of protective shield that enclosures the emitting apparatus hereby reducing the energy that is radiated by the EMR emitting device. Alternative approach is disclosed by Smirnov (U.S. Pat. No. 6,369,399), which describes an EMR shielding material that is composed of an electromagnetic radiation optimum neutralized polymer (MRET-Shield). MRET-Shield material does not reduce the power of electromagnetic fields. It "shields" the cellular structures of the body against the harmful biological effects of EMR. The radiation is still entering the body but the neutralizing effect of MRET-Shield material reduces the adverse effects associated with exposure. However, MRET-Shield required the design of a protective shell that encloses the EMR emitting device. While personal communications devices, such as cell phone or Blackberry, can be easily adapted to fit into such protective shell as a part of their design, enclosing larger electric appliances (inter alia personal computers, game consoles) is often impractical. Further, replacement of current EMR sources such as power lines would be cost prohibitive. Therefore, there remains a need to protect against EMR emitted from devices that do not provide a protective shell.

SUMMARY OF THE INVENTION

The present invention addresses deficiencies in current methods for the protection against electromagnetic radiation and provides related benefits. In one aspect of the present invention a device for protecting a subject against exposure to electromagnetic radiation emitted from a remote source is provided. The device includes a housing, a solenoid operably connected to a driver and a polymer. The solenoid generates incident radiation which results in the polymer emitting electromagnetic oscillations at frequencies that counter adverse effects associated with the subject's exposure to the electromagnetic radiation. In one embodiment, the polymer includes a polar matrix, an oxidated hydrocarbon emulsifier, a galvanic salt, a dye or stain, and a polysaccharide. The solenoid is provided in various configurations. In some embodiments, the solenoid includes a two frequency mode that generates at least one carrier frequency of incident radiation. In other embodiments, the solenoid includes a two frequency mode that generates two carrier frequencies of incident radiation, wherein the carrier frequencies are at higher frequencies than the oscillation frequencies. Carrier frequencies may independently or collectively induce oscillation of the polymer materials. In some embodiments, the solenoid is positioned circumferentially around an inner cylinder that houses the polymer.

The device of the present invention will have particular utility for the protection against radiation emitted from electronic devices such as a computer, a computer peripheral, a cellular telephone, a television, an audio system, a household appliance, and the like. Further, the device may protect against any intentional or unintentional sources of electromagnetic radiation with Effective Radiation Power (ERP) limited in compliance with FCC regulations.

In another aspect of the invention, methods of protecting a subject against exposure to electromagnetic radiation from a remote source are provided. The methods include providing a device as provided by the present disclosure within an effective radius of the subject, and operating the device, such as by activating the solenoid driver. In some embodiments, the device is positioned within a same room as the subject. In other embodiments the device is placed from about five feet to about twenty feet from the subject. In other embodiments, a plurality of devices is provided within a plurality of locations.

BRIEF DESCRIPTION OF THE DRAWINGS

FIG. 4A displays the results from the control test, where the phantom head is exposed to EMR of cellular phone without the MRET Random Field Generator. FIG. 4B displays the test results where the phantom head is exposed to EMR of cellular phone in combination with protective MRET Random Field Generator. A 'hot spot', characterized by the elevated amplitude depicted by darker red, is clearly present in both scans (FIGS. 4A and 4B). Comparing FIGS. 4A and 4B, it is clear that the presence of the protective device does not alter or redistribute the location of the hot spot within the phantom head. However, the amplitudes within the hot spot are decreased in about 80% of data points. About 65% of data points showed significant reduction of SAR values in the range of about 10% to 40%. Thus, the presence of MRET Random Field Generator protective device leaded to the reduction of the majority of SAR values.

DETAILED DESCRIPTION OF THE INVENTION

The present invention addresses deficiencies in current technologies for the protection against electromagnetic radiation and provides related benefits. It is an object of the present invention to provide a device that protects against exposure to electromagnetic radiation. It is another object of the present invention to provide a device that is portable, which allows placement in an area that includes an increased or deleterious amount of EMR. Thus the device may be continuously operated for continued protection against EMR from remote sources.

The present invention protects against remote sources of EMR and is therefore protective against any EMR emitting device operating in frequencies as devices disclosed herein. Non-limiting examples include a computer, a computer peripheral, a cellular telephone, a personal communications device, a television, an audio system, or any household appliance that may intentionally and/or unintentionally emit electromagnetic radiation. The term "remote source" refers to a source of EMR that is remote from the device of the present invention. The present invention may protect against EMR emitted from indoor or outdoor power lines. Accordingly, the device of the present invention may be placed in proximity to the user when operating or exposed to devices that emit EMR. In some embodiments, the device is positioned within the same room as the EMR emitting device and in some embodiments the device protects against EMR emitting devices from different rooms or outdoors. In some embodiments, the device is positioned within about twenty feet from the subject requiring protection; however, the protective distance can be significantly higher when using carrier frequencies discussed herein and the like. Though operable outdoors, the present invention may have particular use indoors to provide protection within an indoor room, such as within a 12×12 square foot room or a 40×20 square foot room. The number of subjects that may be protected with the present device is only limited by the protected area. Thus, a single device may protect a plurality of subjects within the operating area. The area of operation can be increased by increasing the amplitude of the emitted frequencies.

The present invention operates by generating incident radiation, which induces oscillation of a polymer. The oscillation frequencies emitted by the polymer are demonstrated herein to protect users against remote sources of EMR. These emitted protective frequencies prevent or reduce the ordinarily deleterious effect from EMR exposure, such as high frequency EMR, on biological processes. Among the deleterious effects protected against may include changes in viscosity, pressure or water content of bodily fluids such as interstitial fluid, blood, and the like. The present invention may also protect against changes in body pH, oxygen content, hydration, mitochondrial activity, hormone levels and the like. The present invention may prevent or reduce the accumulation of free radicals in response to exposure to EMR. The incident radiation acts as a carrier frequency, which carries oscillations emitted by the polymer; thus delivering protective frequencies to the intended recipient. Alternatively, protective frequencies are generated separate from the incident radiation.

Figure 1A:
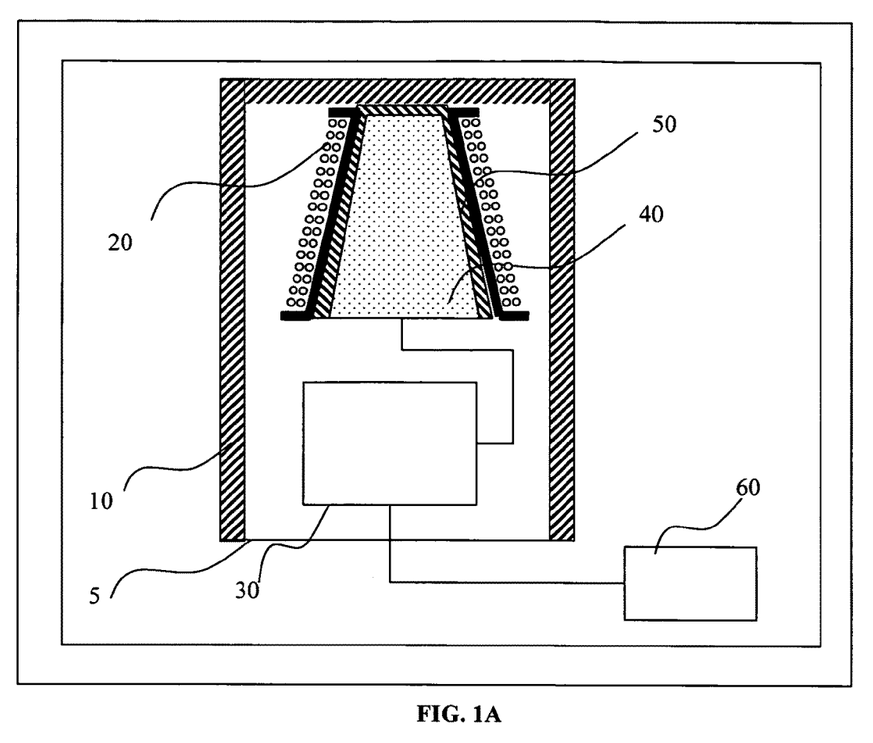
FIG. 1A is a cutaway view of an exemplary embodiment shown in FIG. 1B, including housing 10, a solenoid 20 operably connected to a driver 30, a polymer 40 and a power adapter 60.
Figure 1B:
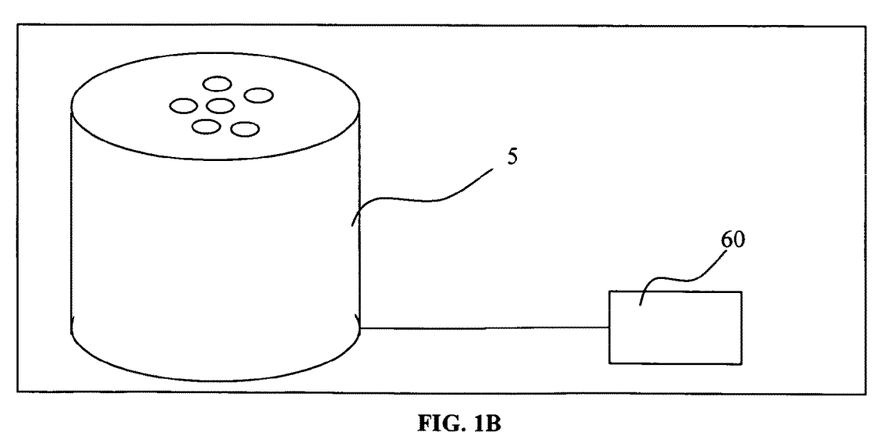

In one aspect of the present invention a device for protecting a subject against exposure to electromagnetic radiation emitted from a remote source is illustrated in FIGS. 1A and 1B. The MRET Random Field Generator device 5 comprises a housing 10 constructed of a plastic material permeable to appropriate frequencies; a solenoid 20 operably connected to a driver circuit 30 and capable of generating incident radiation; and a polymer 40 that upon exposure to the incident radiation emits electromagnetic oscillation frequencies that counter adverse effects associated with the subject's exposure to the electromagnetic radiation. Preferably, the polymer 40 is provided in cylindrical form, such as within a cylindrical shell 50 constructed of a material, preferably plastic, permeable to appropriate frequencies that fits inside the inner circumference of the solenoid 20 as illustrated in FIG. 1A. Although the amount of polymer is non-limiting, a range from about 5 g to about 100 g may be desirable. In a preferred embodiment 34 g of polymer was used. Preferably, the MRET Random Field Generator device is powered by a 12V wall DC power supply 60 as shown in FIG. 1B; however, one skilled in the present art would be able to substitute a suitable power source or power supply.

Referring to FIG. 1A, the solenoid 20 operates at an appropriate current rating to provide suitable incident radiation. As an exemplary embodiment, a solenoid may be constructed from multiple turns of thin wire and in some embodiments may have a current rating of about 300 mA and may have a frequency response adequate for operating in the frequency range between about 7.0 Hz and 15.0 Hz. The experimental data provide evidence of the peak interference spectra for Calcium and Sodium ion transportation for the following applied frequency "windows" of 7.8 Hz and 15 Hz. The housing 10 is constructed of a plastic material permeable to the appropriate incident frequencies.

The protective features of the device 5 may act by targeting or affecting Calcium and/or Sodium ions in the user's body by emitting and optionally carrying the protective frequencies. The device 5 and methods may affect localization of Calcium and/or Sodium ions in the body; ion pumps and/or ion channels; chemical or biological reactions involving the interaction, binding or transfer of Calcium and/or Sodium; and the like. Calcium is very important for the function of the organism. $Ca^{2+}$ ions contribute to the activity of many enzymes, synaptic transfer, secretion, muscular contraction, proliferation, growth and development by interaction with cells or proteins, such as calmodulin and troponin. Sodium ions ($Na^+$) provide for a naturally balanced acid-alkaline medium in the organism and excitation signal transfer processes along the nerve cells. $Na^+$ ions are involved in the function of the "ion pumps" that produce an electrical potential difference across the cell membranes by increasing the density of Sodium in the extracellular medium. The protective effects of the instant invention may affect the localization of ions such as Sodium or Calcium, activity of ion pumps or ion channels, and the like.

The protective features of the device 5 may act by affecting or organizing clathrate structures of the cellular fluids within the body that leads to support of normal biochemistry of intracellular water. By affecting or organizing clathrate structures the instant invention prevents adverse reactions from exposure to EMR.

Figure 2:
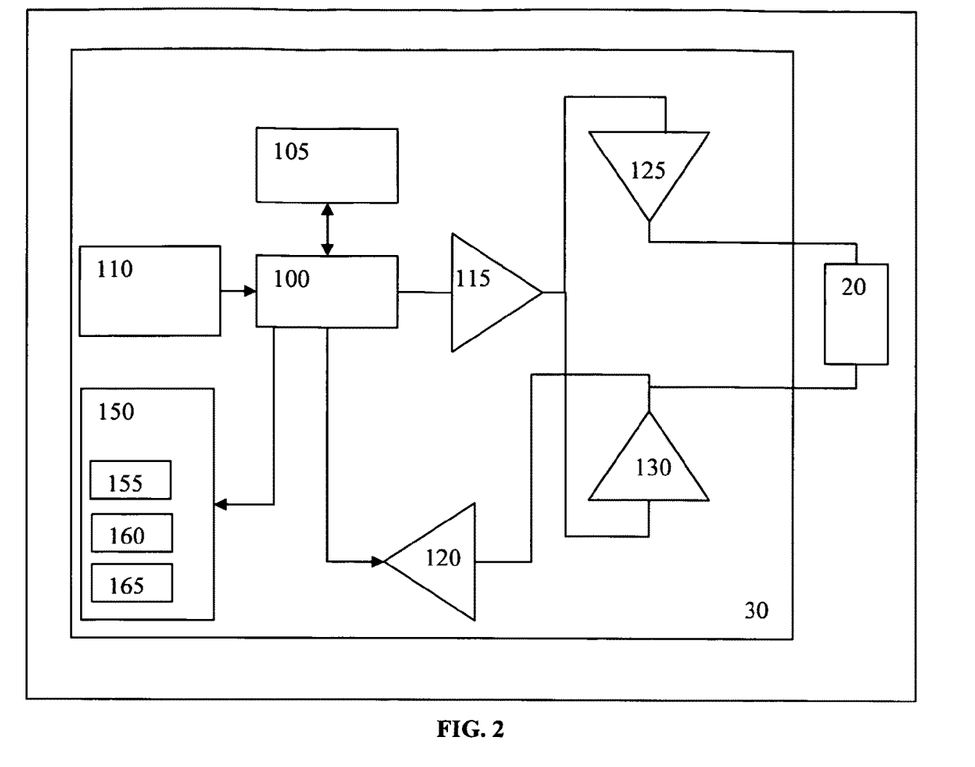
FIG. 2 depicts one exemplary circuit schematic diagram for the generation of incident radiation including carrier frequencies according to the present invention.

The solenoid driver 30 is a microprocessor controlled drive circuit, such as illustrated in FIG. 2, which provides voltage of varying amplitude and frequency to the Solenoid Polymer Assembly. The circuit 30 comprises a microcontroller 100, nonvolatile memory module 105 for storing the operating code, triple DIP switch 110 that controls functions of the solenoid driver, pre amplifier 115, dual power amplifiers 125 and 130 that are operably connected to a driver to solenoid 20, power mode feedback control circuit 120, and status three color LED 150.

The user controls the operation of the solenoid driver 30 preferably by setting individual switches in triple-row DIP switch bank 110. The switch functions are as follows.

The first row of DIP switch 110 has two states RUN and RESET. The RESET is the initial startup mode to ensure the proper initialization of the Solenoid Driver circuit. This function is also used to reset the internal Time of life counter. To reset the counter typically the unit is powered down and powered back up with the switch #1 of the DIP switch bank 110 in the RESET position.

RUN is the normal operation mode and is enabled by setting the switch #1 into RUN position. Once the unit is taken out of the RESET and put into RUN mode the microcontroller will ignore the RESET switch state, except during the power-up period.

The second row of the DIP switch 110 controls current draw of the unit. The LO and the HI switch states correspond to the 140 mA low-current draw and 280 mA high current draw settings respectively. To ensure proper operation of the unit this switch must be left in its state during operation. If current mode change is desired typically the unit is first powered down in order to change the switch state.

The third row of the DIP switch 110 controls frequency mode of operation. The 2F setting denotes the dual-frequency mode of operation. When dual-frequency mode of operation is selected the LOW and the MID frequency components of the incident radiation are being generated by the driver circuit.

In the preferred embodiment, the solenoid driver module features a LED assembly 150; comprising of the three color RGB LED 155, green LED 160 and red LED 165 for providing visual feedback during its operation to the user.

The RGB LED 155 operates as follows: green color indicates that the low frequency of the incident radiation is being generated; yellow color indicates that the MID frequency of the incident radiation is being generated. Red color state of the RGB LED 155 indicates calibration failure. During the power up stage the microcontroller performs calibration procedure where it checks, inter alia, the presence of solenoid, power mode and frequency mode switch settings. If calibration failure occurs, the unit is typically powered down and reset. Once the unit has successfully passes the calibration sequence, the green LED 160 is illuminated for the duration of the unit operation.

The microcontroller records the period of time that the solenoid driver circuit is in operation in a 'Time of Life' counter. The lifetime of useful operation will vary depending on factors such as the particular polymer used and the like. As general guidance, it is estimated that the lifetime of useful operation of the MRET-Shield polymer is approximately 17,000 hours. Accordingly, upon the completion of 17,000 hours the microcontroller may issue a warning to the user by flashing (periodically turning on and turning off) the red LED 165. After an additional 200 hours of operation the red LED may stop blinking and stay illuminated. This indicates 'end of life' of the MRET-Shield polymer and the circuit will stop operating. The times provided are exemplary only.

In the preferred embodiment the polymer of the present invention is the MRET-Shield polar polymeric material disclosed in Smirnov, U.S. Pat. No. 6,369,399 which is incorporated by reference herein in its entirety. In its most basic form the preferred substance is a polymeric material in which the polymeric substance contains small quantities of several components: an oxidized hydrocarbon emulsifier, a galvanic salt, an alkaloid, a dye or stain, and a polysaccharide. Collectively the components form a unique composition that displays a characteristic behavior, when activated by exposure to EMR, to generate its own electromagnetic oscillations at frequencies that resonate with living cellular structure and effectively counteract the harmful aspects of the EMR. The polymer that forms the matrix of the preferred MRET-Shield polymer material can be any polar thermosetting or thermoplastic polymer that has a high value of relative permittivity (dielectric constant). The polymer can be cast into a mold consistent with configurations discussed in the present disclosure.

The EMR shielding material MRET-Shield was proven to produce the biological protective effect. This polar polymer material was tested by Underwriters Laboratories and received a UL recognition mark in March 2001. EMR shielding material does not reduce the intensity (power) of electromagnetic fields. It "shields" the cellular structures of the body against the harmful effects of EMR. The radiation still enters the body but the neutralizing effect of this polar polymer reduces harmful effects associated with EMR. The EMR shielding polar polymer can neutralize negative effects of EMR by changing the quality or effect of the electromagnetic field rather than reducing its power, which provides benefits over alternative approaches. In contrast, devices that claim to reduce the power of electromagnetic fields create distortion of transmitted signals and worsen the reception of cellular phones, because these devices are based on ferromagnetic materials or high density metals. Besides they reduce the radiation only by 15-20%. They also can create even worse problems for the cellular structures of the body because electromagnetic processes in the cells are thousand times weaker then electromagnetic fields generated by any electronic appliances. Taking into consideration that most of the appliances (cellular phones, computers, etc.) are usually located in a very close proximity to the human body, it is reasonable to admit that shielding devices, which reduce electromagnetic fields, first of all will suppress and disturb electromagnetic processes in living cells.

EXAMPLES

Example 1

Electro Interstitial Scan (EIS) Demonstrates MRET Random Field Generator (MARNF) Protects Against EMR Emitted from Commercially Available Cellular Telephone (RF Phone)

EIS analysis was conducted at an independent testing facility to assess the biological effects of electromagnetic radiation from a cellular telephone on the human body and whether effects would differ if providing a MRET random field generator (MARNF) within about 3.3 meters (10 feet) from the subject during cellular telephone use.

Figure 3A:
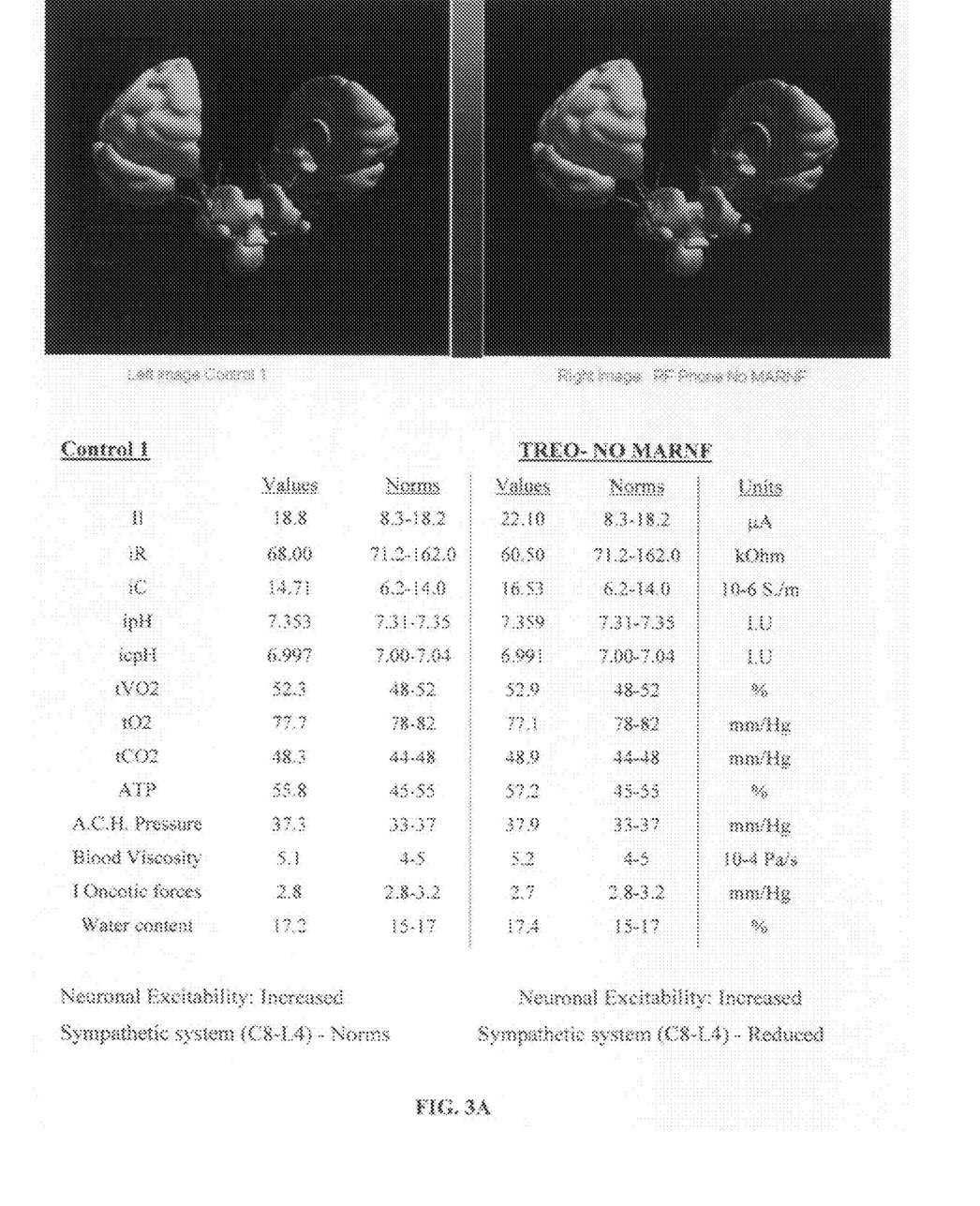
FIG. 3A depicts pictorial images of EIS analysis of the brain and displays the corresponding data tables from EIS testing of a representative subject: Control 1 and after exposure to electromagnetic radiation from a cellular telephone placed in close proximity to the subject's right ear without the protective apparatus of the present invention.
Figure 3B:
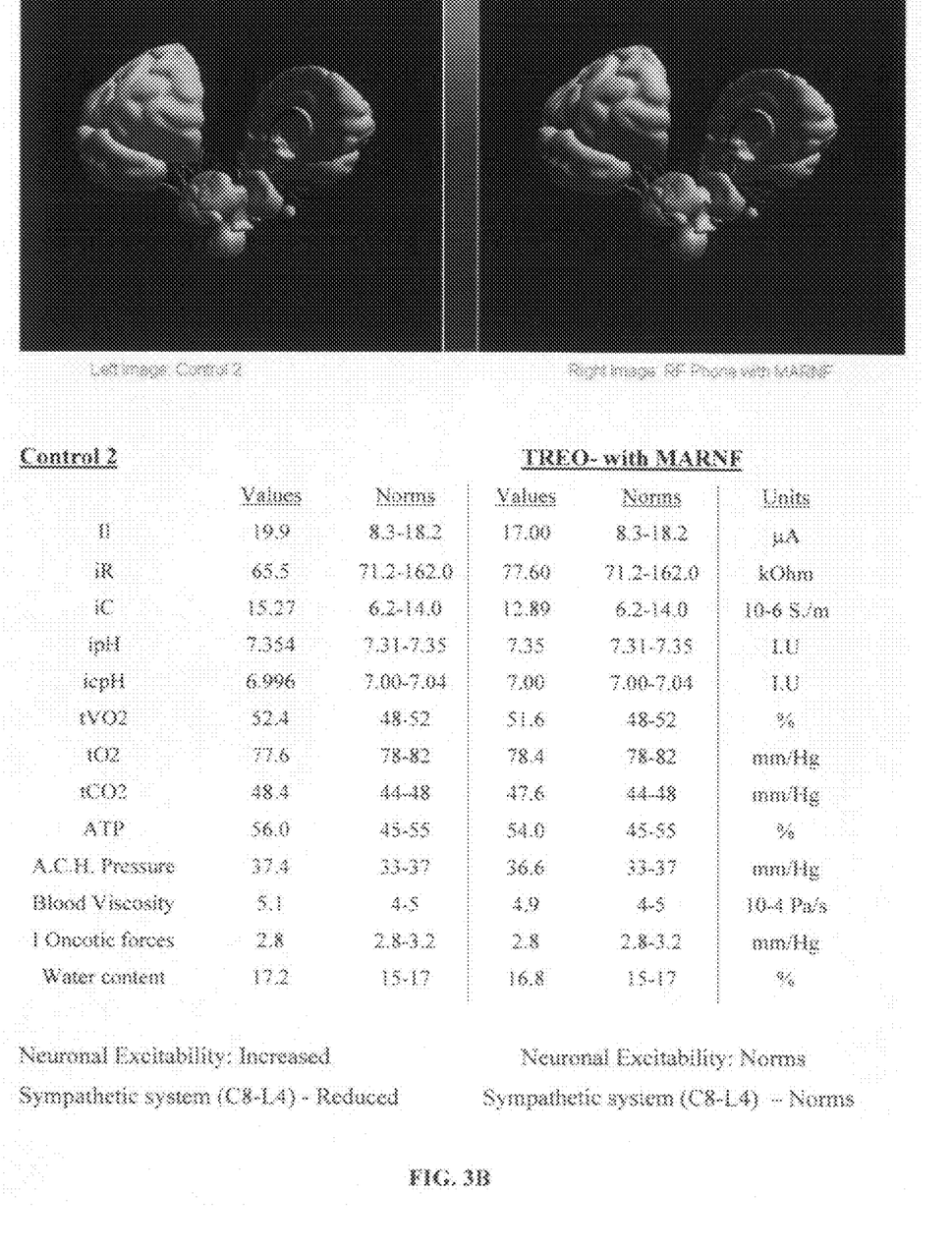
FIG. 3B provides representative data from the same subject: Control 2 and after exposure to electromagnetic radiation from a cellular telephone placed in close proximity to the subject's right ear in combination with the protective apparatus of the present invention. As seen pictorially in FIG. 3A (following the exposure to RF phone without the protective apparatus of the present invention (labeled TREO—NO MARNF), the subject's right frontal lobe showed abnormal values along with the abnormal values from hypothalamus, and they were pictorially displayed as yellow and blue colors respectively. Yellow color corresponds to elevated conductivity, reduced viscosity or acute inflammation and blue color corresponds to decreased conductivity, increased resistance, increased viscosity, organ hypoxia or chronic inflammation. The comparison with experimental data for Control 1 showed that after the exposure to electromagnetic radiation of a cellular phone all parameters deteriorated. However, when using the protective device MARNF of the present invention in combination with the cellular telephone (labeled TREO—with MARNF) the positive effects were identified at the right temporal lobe and more significantly the right frontal lobe (FIG. 3B). After the 15 minutes rest period the second control scan was taken (left image, Control 2). The values of all parameters drifted to the normal state, but did not reach the normal ranges. Following the 10 minutes exposure to RF phone in combination with MARNF (right image, TREO—with MARNF additional positive effects were detected in blood pressure, blood viscosity, ATP values and mitochondrial activity, oxygen levels, carbon dioxide levels and all parameters normalized.
Figure 3C:
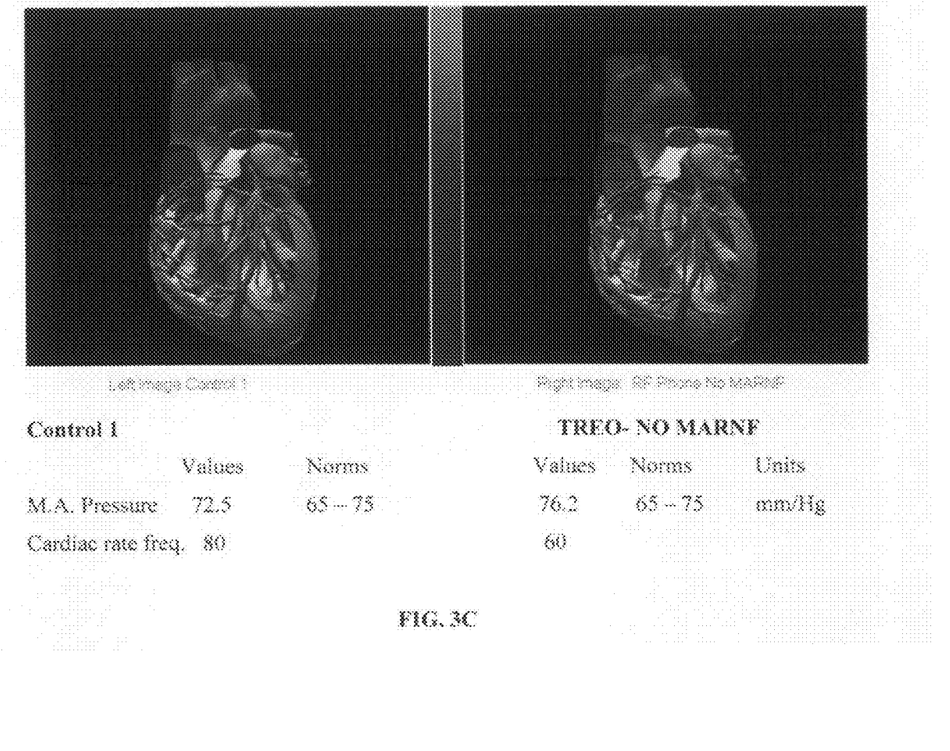
FIG. 3C depicts a pictorial images of EIS analysis of the cardiovascular system and displays the corresponding data tables from EIS testing of a representative subject: Control 1 and after exposure to electromagnetic radiation from a cellular telephone placed in close proximity to the subject's right ear without the protective apparatus of the present invention.
Figure 3D:
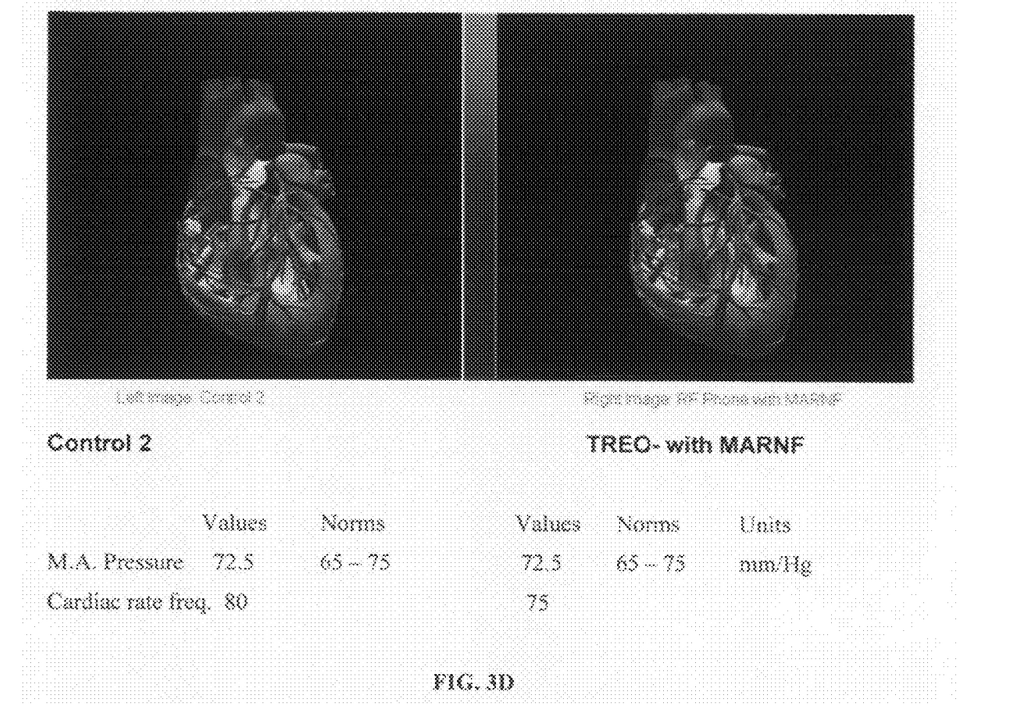
FIG. 3D provides representative data from the same subject: Control 2 and after exposure to electromagnetic radiation from a cellular telephone placed in close proximity to the subject's right ear in combination with the protective apparatus of the present invention. As seen pictorially in FIG. 3C (Control 1) the subject's heart has reduced function in the inferior vena cava and depressed venous pressure. All other cardiac tissue appear remaining normal. After exposure to RF phone, proximal to the subject's right temporal lobe, mean arterial pressure (MAP) rose above normal range activating the baroreceptor reflex, as shown in yellow and blue color (right image, TREO—NO MARNF) and cardiac rate frequency dropped by 25%. However, the positive effects were identified when using the protective device MARNF of the present invention in combination with the cellular telephone (labeled TREO—with MARNF, FIG. 3D). After the fifteen minutes rest period the second control scan was taken (left image, Control 2). The baroreceptor reflex returned to normal values and all cardiac tissue except for the inferior vena cava appear normal. After the ten minutes exposure to RF phone in combination with MRET Random Field Generator (right image, TREO—with MARNF) the mean arterial pressure remained stable and identical to control 2 scan, and cardiac rate frequency dropped insignificantly by 7.5% (compare to 25% drop without MARNF protection).

The color legend for EIS color model images is as follows: grey indicates normal; yellow indicates elevated conductivity, reduced viscosity or acute inflammation; blue indicates decreased conductivity, increased resistance, increased viscosity, organ hypoxia or chronic inflammation. The legend for EIS data provided in tables is as follows: Il-intensity; iR—resistance; iC—conductivity; ipH—interstitial fluid pH; icpH—intercellular pH; $tVO_2$—tissue oxygen volume; $tO_2$—tissue oxygenation; $tCO_2$—tissue $CO_2$; ATP—Mitochondrial production ATP; A.C.H. pressure—arterial capillary hydrostatic pressure; and I oncotic forces—interstitial oncotic pressure; and M.A. Pressure—mean arterial pressure FIG. 3A shows the EIS color model images and corresponding data for Control 1 vs. RF phone without MARNF (labeled TREO—NO MARNF). FIG. 3B shows the EIS color model images and corresponding data for Control 2 vs. RF phone in combination with EMR protective device of present invention MRET Random Field Generator or MARNF (labeled TREO—with MARNF). FIG. 3C shows EIS images and data from the heart corresponding to Control 1 vs. RF phone without MARNF (labeled TREO—NO MARNF). FIG. 3D shows EIS images and data from the heart corresponding to Control 2 vs. RF phone in combination with EMR protective device of present invention MRET Random Field Generator or MARNF (labeled TREO—with MARNF).

SUMMARY OF RESULTS

The test results in FIG. 3A show that the subject displays hyperactivity of the right frontal lobe during Control 1. After 10 minutes exposure to radiation of TREO 650 cellular phone (referred as TREO RF), all parameters demonstrate negative changes (opposite from normal range): intercellular pH (icpH) begins to drop, as interstitial fluid pH (ipH) rose due to the influx of potassium from within the cellular membranes. ATP increased with the applied EMR field, as edema increases and hydrostatic pressure similarity increases to remove the excess of water in the blood vessels. Overall there are negative effects due to proximity to a non-ionizing RF phone. While the hypothalamic region remains mostly within the normal parameters it is becoming hypo-functional in respect to the changes in the function of the sympathetic nervous system (C8-L4). The state of sympathetic nervous system changed from normal to reduced function. Overall there are indications of negative cerebral effects due to exposure to RF phone. The subject's right frontal lobe showed abnormal values along with the abnormal values from hypothalamus, and they were pictorially displayed as yellow and blue colors respectively. Yellow color corresponds to elevated conductivity, reduced viscosity or acute inflammation and blue color corresponds to decreased conductivity, increased resistance, increased viscosity, organ hypoxia or chronic inflammation. Thus, after the exposure to electromagnetic radiation of a cellular phone all parameters deteriorated.

The test results shown on FIG. 3B were taken following the 15 minutes break down. The image and data for Control 2 indicate that the values for the right front lobe began to normalize as a result of rest in the absence of EMR exposure. Based on the previous experience it was expected that this positive trend will be interrupted or reversed upon the re-application of EMR. However, scans taken after 10 minutes exposure to the EMR of TREO RF while simultaneously exposure to MARNF (MRET Random Field Generator) indicate continuing normalization of all parameters within the tissue. Additionally, enervation to the sympathetic nervous system (C8-L4) is improved after exposure to MARNF, despite relative proximity of the TREO RF to the subject's right temporal and frontal lobes. The positive effects were detected also in blood pressure, blood viscosity, ATP values and mitochondrial activity, oxygen levels and carbon dioxide levels when using protective MRET Random Field Generator of the present invention. Results of these scans suggest that MARNF has a measured positive cerebral effect.

Another example shown in FIG. 3C provides pictorial evidence of the measured negative effect of RF phone on the cardiovascular system of the subject. The EIS Control 1 scan indicates reduced function in the inferior vena cava and depressed venous pressure. All remaining cardiac tissue appears normal. After exposure to RF phone, proximal to the subject's right temporal lobe, his mean arterial pressure (MAP) begins to rise, activating the baroreceptor reflex, as shown in yellow (right image). MAP increases from 72.5 for the Control 1 and to 76.2 for TREO—NO MARNF and cardiac rate frequency dropped by 25%. It indicates measured negative cardiovascular effect following the RF phone exposure.

The scan images shown in FIG. 3D provide evidence that the exposure to EMR of RF phone in combination with MRET Random Field Generator (MARNF) has no negative effect on the cardiovascular system of the tested subject. The second control scan of the subject was performed after the fifteen minute rest period. The baroreceptor reflex returned to normal values and all cardiac tissues except for the inferior vena cava appear normal. The image labeled TREO—with MARNF shows the scan after ten minutes exposure to RF phone in combination with MRET Random Field Generator. Mean Arterial Pressure remains stable and identical to Control 2 scan. It indicates positive cardiovascular effect of MRET Random Field Generator and cardiac rate frequency drops insignificantly by only 7.5% (compare to 25% drop without MARNF protection).

Materials and Methods

The experiments detected changes in brain chemistry using Electro Interstitial Scanning (EIS). EIS gives a comprehensive overview of the reactions of the body. 3D models of the full body and various different parts of the body are created based on the electro interstitial gram (EIG). The models are color coded to indicate where areas of imbalance are hyper-functioning or hypo-functioning. In essence, EIS provides a functional assessment of the main organs, with report screens that show interstitial biochemical values and an evaluation of body composition including lean mass, fat mass and hydration data. Measurements are further extrapolated to provide report screens with hormone, electrolyte, neurotransmitter and oxidative stress analyses. More specifically, the EIS system operates as a biosensor, which analyzes the interstitial fluid locally in vivo by application of a D.C. current between cutaneous zones using electrodes. In use, the EIS introduces electric signals of low intensity (1.28V D.C.) through the human body via 6 electrodes. This is painless and has no negative effects to the patient. About 22 measurements are taken. The scanning results are recorded by EIS software, which analyzes and interprets the test results and produces a variety of informative models, graphs and data for interpretation by a medical practitioner.

A TREO 650 cellular telephone (referred to herein as TREO RF), which operates at frequencies of about 1851.25-1908.75 MHz (PCS and CDMA frequencies) was used as a typical source of EMR. The MARNF (MRET Random Field Generator) included a housing, a solenoid operably connected to a driver and a polymer. The polymer included a polar matrix, an oxydated hydrocarbon emulsifier, a galvanic salt, a dye or stain, and a polysaccharide. The present example used 34 g of polymer.

The subject was scanned at four time points. First scan (Control 1) was conducted before any exposure to EMR. Second scan (NO MARNF) was performed after the subject was exposed to the TREO RF, which was placed next to the right ear of the subject. The EIS scan was performed after 10 minutes of exposure to the TREO RF. The thirds scan (Control 2) was conducted after the subject rested for approximately 15 minutes as a second control. The last scan (with MARNF) was taken after the subject was exposed to the same TREO 650 cellular telephone for 10 minutes while simultaneously being exposed to the MARNF protective generator, placed about 3.3 meters (10 feet) away.

Example 2

Figure 4A:
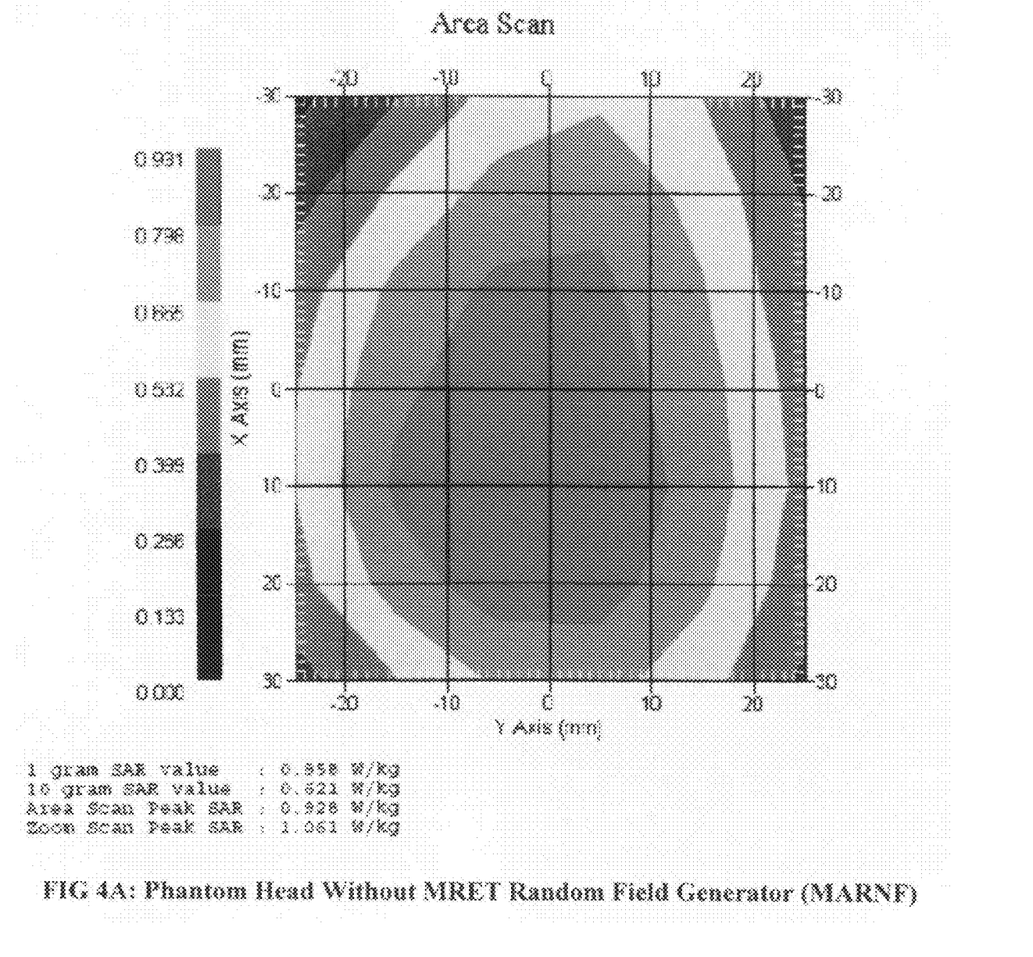
FIGS. 4A and 4B depict heat maps (hot spots) in the "phantom head" during the study which detected SAR (Specific Absorption rate) values of electromagnetic radiation from cellular phone in combination with and without the apparatus of the present invention.
Figure 4B:
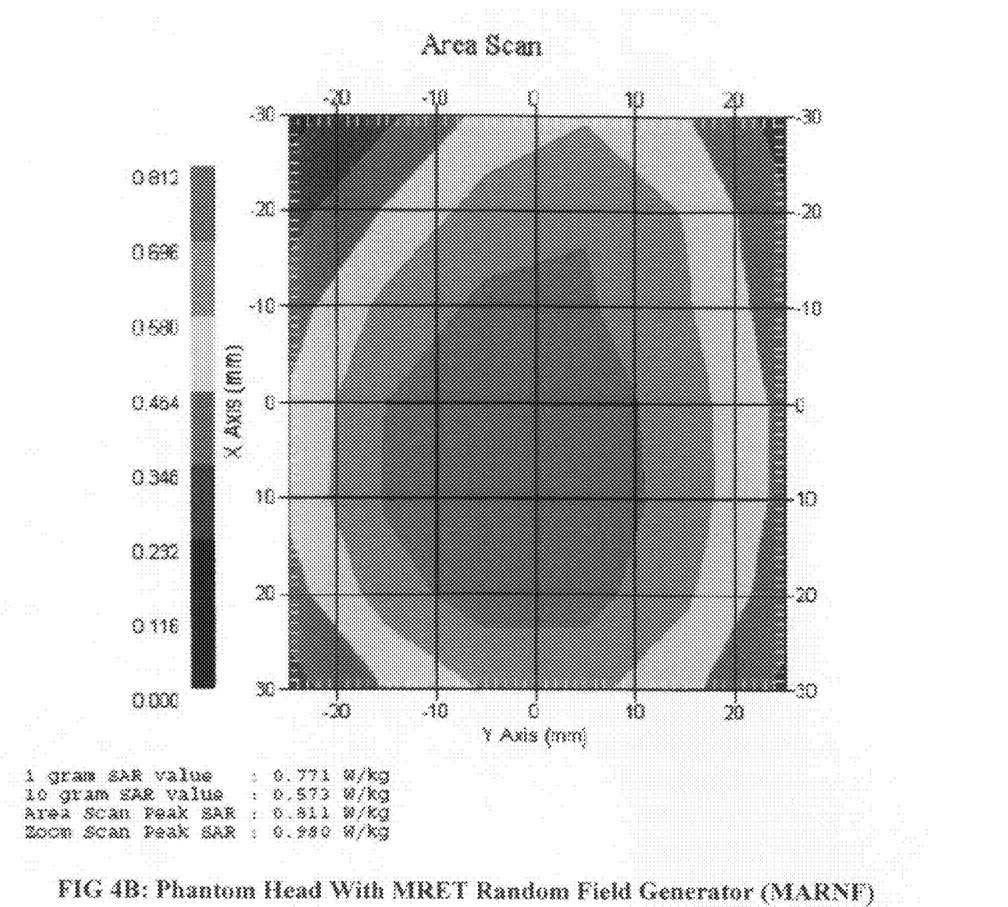

The Demonstration of Protective Effect of MRET Random Field Generator During Exposure of a Phantom Head to Electromagnetic Radiation from a Cellular Telephone The example (depicted in FIGS. 4A and 4B) demonstrates the protective qualities of the present invention by measuring Specific Absorption Rate (SAR) values of electromagnetic radiation absorbed by a "phantom head," which mimics the human head muscle and brain tissue composition. The SAR values were measured and "hot spots" localization of electromagnetic radiation generated by RF phones was investigated. The results in FIG. 4B show a measured reduction of the absorption of electromagnetic radiation by muscle and brain tissue, but no significant shift in localization of "hot spots" which indicates that MRET Random Field Generator successfully reduces potential harmful effects on brain chemistry following the electromagnetic radiation exposure. The study was performed using a variety of wireless RF phones and is described in more details below.

To assess the protective effects of the present invention against exposure to radiation, a "phantom head" was used to mimic the brain and muscle composition within the head. The "phantom head" was produced using a combination of hydroxyethylcellulose (FEC) gelling agent and saline solution. The mixture was calibrated to obtain proper dielectric constant (permittivity) and conductivity of the simulated tissue. The dielectric constant at about 835 MHz was about 40 and at about 1900 MHz, was about 39. The conductivity at about 835 MHz was about 0.88 mho/m, and the conductivity at about 1900 MHz was about 1.43 mho/m. An APREL Laboratories ALSAS system with a dosimetric E-field probe E-020 was used for measurements. The dipole was oriented parallel to the body axis. The investigation was conducted on cellular phones including Qualcomm Model QCP-2035a, Kyocera Wireless Model 2325 and Samsung Model SCH-A670.

Wireless mobile phones were evaluated in this experiment for localized specific absorption rate (SAR) for controlled environment/occupational exposure limits specified in ANSI/EEE Std. C95.1-1992 and had been tested in accordance with the measurement procedures specified in IEEE 1528-2003 and OET Bulletin 65. The RF phone was placed into simulated transmit mode using the manufacturer's test codes. Such test signals offer a consistent means for SAR and are recommended for evaluating of SAR data. Each SAR measurement was taken with a fully charged battery. In order to verify that each phone was tested at full power, conducted output power measurements were performed before and after each SAR test to confirm the output power. SAR measurement results were obtained, analyzed and compared to provide the scientific conclusion of the experiment: These measurements are taken to simulate the RF exposure effects under worst-case conditions. Precise laboratory measures were taken to assure repeatability of the tests. The tested device complies with the requirements in respect to all parameters subject to the test. The installation and function of MRET Random Field Generator at the distance of 7 feet from the "phantom head" does not significantly affect the air measurements of the RF phone signals and subsequently does not lead to any significant distortion of transmitted RF signals. In each experiment, SAR values were measured in 242 points around the phone within the "phantom head." The effect of MRET Random Field Generator on the "phantom head" showed that the "hot spots" remained in the same location as without MRET Random Field Generator and the amplitudes decreased in 80% of the data points. In 65% of the data points there was observed a significant decrease of SAR values in the range of 10% to 40%. The installation and function of MRET Random Field Generator at the distance of 7 feet from the "phantom head" leads to the reduction of the majority of SAR values.

What is claimed is:

1. A device for protecting a subject against exposure to electromagnetic radiation emitted from a remote source, the device comprising:
   a) a housing;
   b) a solenoid operably connected to a driver, said solenoid capable of generating incident radiation; and
   c) a polymer comprising:
      i. a polar matrix,
      ii. an oxydated hydrocarbon emulsifier,
      iii. a galvanic salt,
      iv. a dye or stain, and
      v. a polysaccharide;
   wherein upon exposure to said incident radiation, said polymer emits random electromagnetic oscillation frequencies that counter adverse effects associated with the subject's exposure to the electromagnetic radiation.

2. The device according to claim 1, wherein said solenoid comprises a two frequency mode that generates two carrier frequencies of incident radiation.

3. The device according to claim 1, wherein said solenoid comprises a two frequency mode that generates two carrier frequencies of incident radiation, wherein said carrier frequencies are higher than said oscillation frequencies.

4. The device according to claim 1, wherein said driver is a Microprocessor controlled drive circuit.

5. The device according to claim 1, wherein said polymer is housed within an inner cylinder, further wherein said solenoid is positioned around the circumference of said inner cylinder.

6. The device according to claim 1, wherein said remote source is selected from the group consisting of a computer, a computer peripheral, a cellular telephone, a personal communications device, a television, an audio system and a household appliances.

7. The device according to claim 1, wherein said remote source is selected from the group consisting of any intentional and/or unintentional sources of electromagnetic radiation with Effective Radiation Power (ERP) limited in compliance with FCC Regulations.

8. A method of protecting a subject against exposure to electromagnetic radiation emitted from a remote source, the method comprising providing the device according to claim 1 within an effective radius of the subject and driving said solenoid.

* * * * *